US010813973B2

(12) United States Patent
Kim et al.

(10) Patent No.: US 10,813,973 B2
(45) Date of Patent: Oct. 27, 2020

(54) COMPOSITION COMPRISING THE EXTRACT OF HERBAL COMBINATION FOR PREVENTING OR TREATING DIABETIC PERIPHERAL NEUROPATHY

(71) Applicant: DONG-A ST CO., LTD., Seoul (KR)

(72) Inventors: Soon-Hoe Kim, Suwon-si (KR); Mi-Won Son, Yongin-si (KR); Sang-Zin Choi, Yongin-si (KR); Hye-Ju Kim, Hwaseong-si (KR); Ja-Young Ryu, Seoul (KR); Sun-Yeou Kim, Seoul (KR)

(73) Assignee: DONG-A ST CO., LTD., Seoul (KR)

( * ) Notice: Subject to any disclaimer, the term of this patent is extended or adjusted under 35 U.S.C. 154(b) by 541 days.

(21) Appl. No.: 15/484,067

(22) Filed: Apr. 10, 2017

(65) Prior Publication Data

US 2017/0209515 A1    Jul. 27, 2017

Related U.S. Application Data

(62) Division of application No. 14/003,087, filed as application No. PCT/KR2011/010294 on Dec. 29, 2011, now abandoned.

(30) Foreign Application Priority Data

Mar. 16, 2011   (KR) ........................ 10-2011-0023564

(51) Int. Cl.

| A61K 36/8945 | (2006.01) |
| A23L 33/105 | (2016.01) |
| A23L 2/52 | (2006.01) |
| A61K 9/00 | (2006.01) |
| A61K 9/08 | (2006.01) |
| A61K 9/20 | (2006.01) |
| A61K 9/48 | (2006.01) |

(52) U.S. Cl.
CPC ............ *A61K 36/8945* (2013.01); *A23L 2/52* (2013.01); *A23L 33/105* (2016.08); *A61K 9/0019* (2013.01); *A61K 9/08* (2013.01); *A61K 9/20* (2013.01); *A61K 9/48* (2013.01); *A23V 2002/00* (2013.01); *A61K 2236/15* (2013.01); *A61K 2236/333* (2013.01); *A61K 2236/51* (2013.01); *A61K 2236/53* (2013.01)

(58) Field of Classification Search
CPC .................................................. A61K 36/8945
See application file for complete search history.

(56) References Cited

U.S. PATENT DOCUMENTS

| 8,202,554 | B2 | 6/2012 | Kim et al. ............... 424/725 |
| 2009/0041865 | A1 | 2/2009 | Kim et al. ............... 424/725 |
| 2013/0072459 | A1 | 3/2013 | An et al. ................ 514/81 |
| 2013/0085160 | A1 | 4/2013 | Kim et al. .............. 546/229 |
| 2013/0296571 | A1 | 11/2013 | Son et al. ............... 546/75 |
| 2013/0317052 | A1 | 11/2013 | Son et al. .............. 514/289 |
| 2014/0044817 | A1 | 2/2014 | Kim et al. ............... 424/773 |
| 2014/0155609 | A9 | 6/2014 | Son et al. ............... 546/75 |
| 2018/0318377 | A1 | 11/2018 | Kim et al. |

FOREIGN PATENT DOCUMENTS

| KR | 10-2007-0018570 | 2/2007 |
| KR | 10-0811683 | 3/2008 |
| KR | 10-0854621 | 8/2008 |
| KR | 10-2010-0002668 | 1/2010 |
| KR | 10-2010-0084926 | 7/2010 |
| WO | WO 2007/049932 | 5/2007 |
| WO | WO 2012/124888 | 9/2012 |

OTHER PUBLICATIONS

Letter/Written Disclosure of the Information Disclosure Statement for the above-referenced application, filed herewith on Jun. 9, 2017, 2 pages.
Apfel, S., "Neurotrophic factors in the therapy of diabetic neuropathy," Am. J. Med. 107(2B):34S-42S (1999).
Arrieta et al., "Retinoic acid increases tissue and plasma contents of nerve growth factor and prevents neuropathy in diabetic mice," European Journal of Clinical Investigation 35(3):201-207 (2005).
Choi et al., "Novel botanical drug for the treatment of diabetic neuropathy," Arch. Pharm. Res. 34(6):865-857 (2011).
Cole, B., "Diabetic peripheral neuropathic pain: recognition and management," Pain Medicine 8(S2):S27-S32 (2007).
Dawbarn et al., "Neurotrophins and neurodegeneration," Neuropathology and Applied Neurobiology, 29(3):211-230 (2003).
Dong-A Group website, "Pipeline," Copyright 2009 [online][retrieved on Jul. 7, 2013] Retrieved from:<URL:en.donga.co.kr/rnd/rnd03.jsp, 2 pages.
Dong-A Group website, "R&D at Dong-A," Copyright 2009 [online] [retrieved on Jul. 7, 2013] Retrieved from:<URL:en.donga.co.kr/rnd/rnd01.jsp, 1 page.
Dong-A Group website, "Research Center," Copyright 2009 [online][retrieved on Jul. 7, 2013] Retrieved from:<URL:en.donga.co.kr/rnd/rnd02.jsp, 2 pages.
Eglen et al., "Central 5-HT 4 receptors," Trends in Pharmacol. Sci. 16:391-398 (1995).

(Continued)

*Primary Examiner* — Amy L Clark
(74) *Attorney, Agent, or Firm* — Sterne, Kessler, Goldstein & Fox P.L.L.C.

(57) ABSTRACT

Disclosed are a pharmaceutical composition and a health functional food for the prevention and treatment of diabetic peripheral neuropathy, comprising an herb extract of a mixture of 3.5:1 *Dioscorea* Rhizoma:*Dioscorea nipponica* (w/w). Having the ability to synergistically increase in vivo levels of nerve growth factor, compared to the extracts from the herbs alone or herb mixtures of other weight ratios, the mixed herb extract is effective for preventing the apoptosis of nerve cells and promoting nerve regeneration. Thus, it can be applied to pharmaceutical compositions and health functional foods preventive and curative of diabetic peripheral neuropathy.

16 Claims, 1 Drawing Sheet

(56) References Cited

OTHER PUBLICATIONS

English language abstract of Korean Patent No. KR 10-0811683 (Korean Patent Application No. 10-2006-0115301), Korean Intellectual Property Office, 2 pages.
English language abstract of Korean Patent Publication No. KR 10-2007-0018570 (Korean Patent Application No. KR 10-2005-0073381) Korean Intellectual Property Office, 2 pages.
English language abstract of Korean Patent Publication No. KR 10-2010-0002668 (Korean Patent Application No. KR 10-2008-0062643) Korean Intellectual Property Office, 2 pages.
English language abstract of Korean Patent Publication No. KR 10-2010-0084926 (Korean Patent Application No. KR 10-2009-0004334) Korean Intellectual Property Office, 2 pages.
Ji et al., "Evaluation of DA-9801, a new herbal drug for diabetic neuropathy, on metabolism-mediated interaction," Arch. Pharm. Res. 36(1):1-5 (2013).
Kang et al., "Characteristics of antidiabetic effects of Dioscorea rhizoma(2)—Prevention of Diabetic Neuropathy by NGF Induction—" Korean J. Food & Nutr. 21 (4):430-435 (2008) [article in Korean; includes an English Language abstract].
Kang et al., "Diosgenin from Dioscorea nipponica ameliorates diabetic neuropathy by inducing nerve growth factor," Biological and Pharmaceutical Bulletin 34(9):1493-1498 (2011).
Kim et al., "Furostanol saponins from the rhizomes of Dioscorea japonica and their effects on NGF induction," Bioorganic & Medicinal Chemistry Letters 21(7):2075-2078 (2011).
Kim et al., "Neurotrophic activity of DA-9801, a mixture extract of Dioscorea japonica Thunb. and Dioscorea nipponica Makino, in vitro," Journal of Ethnopharmacology 137(1):312-319 (2011).
Rubino et al., "Diagnosis of diabetic peripheral neuropathy among patients with type 1 and type 2 diabetes in France, Italy, Spain, and the United Kingdom," Primary Care Diabetes 1(3):129-134 (2007).
Song et al., "Evaluation of the transporter-mediated herb-drug interaction potential of DA-9801, a standardized dioscorea extract for diabetic neuropathy, in human in vitro and rat in vivo," BMC Complement Altern. Med. 14:251 (2014).
The Diabetes Control and Complications Trial Research Group, "The effect of intensive treatment of diabetes on the development and progression of long-term complications in insulin-dependent diabetes mellitus," N. Engl. J. Med. 329:977-986 (1993).
Varkonyi, T. And P. Kempler, "Diabetic neuropathy: new strategies for treatment," Diabetes Obes. Metab. 10(2):99-108 (2008).
Wong et al., "Effects of treatments for symptoms of painful diabetic neuropathy: systematic review," BMJ 335(7610):87, 10 pages (2007).
Yang et al., "Phytochemical and pharmacological profiles of Dioscorea species in Korea, China and Japan," Korean Journal of Pharmacognosy 40(4):257-279 (2009) [article in Korean; includes an English Language abstract].
International Search Report and Written Opinion, dated Aug. 31, 2012, in connection with International Patent Application No. PCT/KR2011/010290, 6 pages.
International Search Report and Written Opinion, dated Aug. 31, 2012, in connection with International Patent Application No. PCT/KR2011/010294, 6 pages.
International Preliminary Report on Patentability, dated Sep. 17, 2013, in connection with International Patent Application No. PCT/KR2011/010290, 4 pages.
International Preliminary Report on Patentability, dated Sep. 17, 2013, in connection with International Patent Application No. PCT/KR2011/010294, 4 pages.
Extended European Search Report, dated Jul. 23, 2014, in connection with European Patent Application No. 11861135.9, 7 pages.
Office Action, dated Dec. 31, 2015, in connection with U.S. Appl. No. 14/003,077, 10 pages.
Response, filed Apr. 29, 2016, to Office Action, dated Dec. 31, 2015, in connection with U.S. Appl. No. 14/003,077, 27 pages.
Office Action, dated Jan. 12, 2016, in connection with U.S. Appl. No. 14/003,087, 10 pages.
Extended European Search Report, dated Jul. 28, 2014, in connection with European Patent Application No. 11860864.5, 7 pages.
Decision to Grant a European Patent Pusuant to Article 97(1) EPC, dated Mar. 24, 2016, in connection with European Patent Application No. 11861135.9, 2 pages.
Decision to Grant a European Patent Pusuant to Article 97(1) EPC, dated Mar. 24, 2016, in connection with European Patent Application No. 11860864.5, 2 pages.
Response, filed May 2, 2016, to Office Action, dated Jan. 12, 2016, in connection with U.S. Appl. No. 14/003,087, 22 pages.
Final Office Action, dated Aug. 3, 2016, in connection with U.S. Appl. No. 14/003,087, 16 pages.
Final Office Action, dated Aug. 4, 2016, in connection with U.S. Appl. No. 14/003,077, 16 pages.
Request for Continued Examination and Preliminary Amendment, filed Nov. 3, 2016, in response to Final Office Action, dated Aug. 4, 2016 in connection with U.S. Appl. No. 14/003,077, 20 pages.
Request for Continued Examination and Preliminary Amendment, submitted Nov. 3, 2016, in response to Final Office Action, dated Aug. 3, 2016, in connection with U.S. Appl. No. 14/003,087, 21 pages.
Office Action, dated Jan. 11, 2017, in connection with U.S. Appl. No. 14/003,077, 16 pages.
Office Action, dated Jan. 13, 2017, in connection with U.S. Appl. No. 14/003,087, 16 pages.
Huck et al. "Ribose-5-phosphate isomerase deficiency: new inborn error in the pentose phosphate pathway associated with a slowly progressive leukoencephalopathy," Am. J. Hum. Genet. 74:745-751, United States (2004).
Rowe et al. "Handbook of Pharmaceutical Excipients," Sixth Edition, pp. 596-598 and 654-656; Pharmaceutical Press, England (2009).

COMPOSITION COMPRISING THE EXTRACT OF HERBAL COMBINATION FOR PREVENTING OR TREATING DIABETIC PERIPHERAL NEUROPATHY

RELATED APPLICATIONS

This application is a divisional of co-pending U.S. patent application Ser. No. 14/003,087, lodged on Sep. 4, 2013 and having a 371(c) date of Oct. 3, 2013, which is the U.S. national stage of International Application No. PCT/KR2011/010294, having an international filing date of Dec. 29, 2011, which claims priority to Korean Patent Application No. 10-2011-0023564, filed Mar. 16, 2011, the subject matter of each of which is incorporated by reference in its entirety.

TECHNICAL FIELD

The present invention relates to a composition for the prophylaxis and therapy of diabetic peripheral neuropathy, comprising a herbal extract of a mixture of 3.5:1 *Dioscorea* Rhizoma:*Dioscorea nipponica* (w/w).

ACKNOWLEDGEMENT

This work was supported by the Global Leading Technology Program of the Office of Strategic R&D Planning (OSP) funded by the Ministry of Knowledge Economy, Republic of Korea. (No. 10039303).

BACKGROUND ART

The incidence of diabetes mellitus is rapidly increasing worldwide. The World Health Organization estimated that approximately 180 million people are suffering from diabetes mellitus as of 2008, with the prospect of the number of diabetics doubling by 2030. Accordingly, the financial and social costs associated with diabetes have risen, and there has been an increase in mortality from the complications of diabetes. However, the onset or progression of diabetes can be retarded by strict management of the blood sugar level, so that it is important to keep euglycemia with lifestyle modification and adequate treatment.

Diabetes mellitus is the leading known cause of neuropathy in developed countries. Diabetic peripheral neuropathy is the term used to describe symptoms according to the diabetes-induced dysfunction of the peripheral nervous system. It is the most common complication that diabetics encounter.

Diabetic peripheral neuropathy deteriorates the quality of life of diabetes patients and is the greatest source of patient mortality. The prevalence of diabetic peripheral neuropathy in diabetes patients increases with the age of the patient and the duration of diabetes. Diabetic peripheral neuropathy occurs in both type 1 and type 2 diabetes patients with higher prevalence in type 2 diabetes patients (32.1%) than in type 1 diabetes patients (22.7%) (Primary Care Diabetes Volume 1, Issue 3, September 2007, Pages 129-134, Diagnosis of diabetic peripheral neuropathy among patients with type 1 and type 2 diabetes in France, Italy, Spain, and the United Kingdom).

Approximately 10% of diabetes patients complain of constant pain, which may be spontaneous or may be induced by stimuli. The pain may worsen and become incurable. Diabetic peripheral neuropathic pain is severer typically at night and is described primarily as being a burning discomfort, a stingy ache, sore, straining feeling, and the like. Further, diabetic peripheral neuropathic pain is more often felt in the legs than in the hands. Often, severe pain may lead to weight loss or depression (Pain Medicine, Volume 8 Number S2 2007, Diabetic Peripheral Neuropathic Pain: Recognition and Management).

Diabetic peripheral neuropathy is diagnosed by a muscular strength test, and by measuring tactile sensation, temperature sensation, vibratory sensation, blood flow rate of peripheral skin, and nerve conduction. Diabetic peripheral neuropathy is currently treated by controlling the blood sugar level, etiological treatment, and symptomatic treatment. Because the correlation between hyperglycemia and the progression of neuropathy is well established and has been revealed by many studies delineating the high prevalence rates of diabetic peripheral neuropathy in diabetes patients who have not kept their blood sugar under control, controlling the blood sugar is recognized as a primary method of prevention/treatment of diabetic peripheral neuropathy (N Engl J Med 1993; 329:977-86. The effect of intensive treatment of diabetes on the development and progression of long-term complications in insulin-dependent diabetes mellitus).

Representative among the etiological therapeutics of diabetic neuropathy are alpha lipoic acid, aldose reductase inhibitors, and gamma linoleic acid. α-Lipoic acid (thioctic acid), an antioxidant, reduces the hyperglycemia-induced oxidative stress which leads to the death of nerve cells, thereby blocking the etiology of diabetic neuropathy. Functioning to prevent glucose from entering the polyol pathway in nerve cells, aldose reductase inhibitors can suppress the accumulation of sorbitol, which leads to nerve cell damage, to block the progression of diabetic neuropathy. However, the development of most of them was stopped halfway due to side effects and insufficient efficacy. Currently, only Epalrestat is utilized in Japan. Y-Linolenic acid, which is both a component of nerve membrane phospholipids and a component of prostaglandin E, which plays an important role in the homeostasis of blood flow in nerve cells, is found to ameliorate some symptoms of diabetic neuropathy (BMJ. 2007 Jul. 14; 335(7610):87. Epub 2007 Jun. 11, Review. Effects of treatments for symptoms of painful diabetic neuropathy: systematic review).

Symptomatic therapeutics for alleviating the pain of diabetic neuropathy include tricyclic antidepressants, anticonvulsants, selective serotonin reuptake inhibitors, and topical capsaicin. Tricyclic antidepressants (TCAs) act to inhibit the reuptake of serotonin and norepinephrine in the central nervous system to block the transmission of pain as well as raising the level of endogenous endorphin to alleviate pain. Anticonvulsants and selective serotonin reuptake inhibitors are used as alternatives for patients who are incompatible with TCAs. Topical capsaicin, known to be useful for painful dysesthesia, triggers the release of the neuropeptide, substance P from type-C nociceptive fibers and suppresses the replenishment of substance P to interrupt with the conduction and propagation of peripheral pain signals, which results in a reduction in pain.

However, it is difficult to find therapies that adequately treat patients with diabetic peripheral neuropathy because there is a high versatility of etiologies and symptoms. In practice, symptomatic treatment for alleviating pain and suppressing the progression of diabetic peripheral neuropathy is given preference over etiological treatment. Therefore, there is an increasing need for a therapy that can cure diabetic peripheral neuropathy by regenerating the diabetes-disrupted nerves. Nerve growth factor, functioning to facilitate the regeneration of neurons, is arising as a potent candidate for the therapy of diabetic peripheral neuropathy.

Many previous studies indicate that both the biosynthesis of nerve growth factor and the retrograde transport on neurons in subjects with diabetes are decreased, and so these are regarded as one etiology of diabetic peripheral neuropathy. In healthy persons, NGF is produced in dermal keratinocytes and interacts with the trkA receptor. On the other hand, a low level of NGF is observed in the dermal keratinocytes of diabetes patients, which is known to be associated with the decompensation of sensory nerve fibers (Diabetes Obes Metab. 2008 February; 10(2):99-108. Epub 2007 Jun. 26, Review. Diabetic neuropathy: new strategies for treatment).

Previous studies showed that the administration of NGF brought about a reduction in the pain and symptoms of diabetic peripheral neuropathy-induced animals. Based on this result, clinical trials have also been conducted on patients with diabetic neuropathy. In randomized placebo-controlled, phase 2 clinical trial, the symptoms and pain of patients with diabetic peripheral neuropathy were alleviated after being administered with recombinant human NGF three times/week over 6 months. However, a randomized placebo-controlled, phase 3 clinical trial was conducted over 48 weeks yet was not significantly effective due to pain at the injection site and insignificant pharmaceutical effects. Thus, subsequent studies have been directed toward the promotion of the biosynthesis of endogenous NGF rather than the feeding of external NGF (Am J Med. 1999 Aug. 30; 107(2B):34S-42S, Review. Neurotrophic factors in the therapy of diabetic neuropathy).

Dioscorea Rhizoma, a plant belonging to Dioscoreaceae, is the term for fresh rhizome of Dioscorea batatas Decaisne or Dioscorea japonica Thunberg, void of periderm, or for that obtained after the fresh rhizome was steamed and dried in the herbal medicine. The plant contains the sterol-type saponin dioscin, and allantoin.

Dioscorea nipponica, a rhizome of the climbing perennial plant Dioscorea nipponica Makino, contains various sterol-type saponins, including dioscine, prosapogen A, and prosapogen C.

In herbal medicine, these herbs have been used alone or in combination with other herbs. Nowhere has the medicinal efficacy of an extract from a combination of these two herbs on diabetic peripheral neuropathy been reported in previous documents.

Korean Patent No. 854621 provides a composition for the prevention and treatment of peripheral neuropathy, comprising an extract from a plant selected from among Dioscorea nipponica, Dioscorea quinqueloba, Dioscorea batatas, Dioscorea japonica and Dioscorea tokora, disclosing that the composition induces the growth of neurites and increases the secretion of endogenous nerve growth factor, thus being effective for preventing and treating peripheral neuropathy.

The present inventors confirmed that the function of the extract from a plant selected from among Dioscorea nipponica, Dioscorea quinqueloba, Dioscorea batatas, Dioscorea japonica and Dioscorea tokora was to induce the significant growth of neurites and to increase the secretion of endogenous NGF as disclosed in Korean Patent No. 854621. Surprisingly, the present inventors found through animal model experiments that an extract from a mixture of Dioscorea Rhizoma and Dioscorea nipponica at a specific ratio guarantees therapeutically synergistic effects on diabetic peripheral neuropathy by raising the level of NGF in vivo, e.g., in plasma and in the salivary gland, to a highly significant degree, and by alleviating diabetic neuropathy-induced pain highly sensitive to thermal and mechanical stimuli while extracts from each or a combination of these herbs have almost the same effects in terms of the growth of neurites and the secretion of endogenous nerve growth factor, which culminated in the present invention.

DISCLOSURE OF INVENTION

Technical Problem

It is an object of the present invention to provide a herbal composition, derived from the herbs disclosed in Korean Patent No. 854621, exhibiting the activity of significantly raising in vivo the level of nerve growth factor (NGF) therapeutically effective for diabetic peripheral neuropathy.

It is another object of the present invention to provide a pharmaceutical composition and a health functional food for the prophylaxis and therapy of diabetic peripheral neuropathy, comprising the herbal composition.

Solution to Problem

The objects of the present invention may be accomplished by a provision of a pharmaceutical composition and a health functional food, comprising a herbal extract made from a mixture of 3.5:1 (w/w) of Dioscorea Rhizoma:Dioscorea nipponica useful for preventing and treating diabetic peripheral neuropathy.

In accordance with an aspect thereof, the present invention provides a herbal extract from a mixture of Dioscorea Rhizoma and Dioscorea nipponica. More particularly, the herbal extract provided by the present invention is obtained from a mixture containing Dioscorea Rhizoma and Dioscorea nipponica at a weight ratio of 3.5:1 (w/w).

The herbal extract according to the present invention may be prepared from a mixture of dried Dioscorea Rhizoma and Dioscorea nipponica by cold precipitation in 50% ethanol at room temperature for 48 hours, followed by concentration in a vacuum. In detail, Dioscorea Rhizoma and Dioscorea nipponica are washed, dried, cut, and mixed at a weight ratio of 3.5:1 Dioscorea Rhizoma:Dioscorea nipponica, and the herb mixture is cold-precipitated once in 5 weights of 50% ethanol at room temperature for 48 hours, followed by concentrating the extract at a reduced pressure.

In accordance with another aspect thereof, the present invention provides a composition for the prophylaxis and therapy of diabetic peripheral neuropathy, comprising a herbal extract from a mixture of 3.5:1 Dioscorea Rhizoma: Dioscorea nipponica (w/w) as an active ingredient in combination with a pharmaceutically acceptable carrier, diluents or excipient.

The composition according to the present invention contains the herbal extract from a mixture of 3.5:1 Dioscorea Rhizoma:Dioscorea nipponica (w/w) in an amount of from 0.01 to 80% by weight based on the total weight of the composition, and preferably in an amount of from 1 to 50% by weight.

It should be apparent to those skilled in the art that the symptoms of diabetic neuropathy include the loss of sensation, such as tactile sensation, vibratory sensation, temperature sensation, etc., and pain, such as burning discomfort, stingy aches, soreness, a straining feeling, and the like.

The composition based on a herbal extract from a mixture of 3.5:1 Dioscorea Rhizoma:Dioscorea nipponica (w/w) in accordance with the present invention may further comprise a suitable carrier, excipient or diluent.

Examples of the carrier, excipient or diluents useful in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

The composition of the present invention may be formulated into oral dosage forms such as powders, granules, tablets, capsules, suspensions, emulsions, syrups, aerosol, etc., topical agents, suppositories, or sterile injection solutions. The pharmaceutical composition of the present invention may be formulated in combination with a diluent or excipient, such as a filler, a thickening agent, a binder, a wetting agent, a disintegrant, a surfactant, etc. Solid preparations intended for oral administration may take the form of tablets, pills, powders, granules, capsules, and the like. In regards to these solid agents, the combined herbal extract of the present invention is formulated in combination with at least one excipient such as starch, calcium carbonate, sucrose, lactose, or gelatin. In addition to such simple excipients, lubricants such as magnesium stearate and talc may be used. Liquid preparations intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid preparations. Also, the pharmaceutical composition of the present invention may be administered via a non-oral route. For this, sterile aqueous solutions, non-aqueous solvents, suspensions, emulsions, lyophilizates, suppositories, and the like may be used. Injectable propylene glycol, polyethylene glycol, vegetable oils such as olive oil, and esters such as ethyl oleate may be suitable for non-aqueous solvents and suspensions. The basic materials of suppositories include Witepsol, macrogol, Tween 61, cacao butter, laurin butter, and glycerogelatin.

In accordance with a further aspect thereof, the present invention provides the use of the herbal extract from a mixture of 3.5:1 *Dioscorea* Rhizoma:*Dioscorea nipponica* (w/w) in preparing a therapeutic agent for diabetic peripheral neuropathy.

In accordance with still a further aspect thereof, the present invention provides a method for treating diabetic neuropathy, comprising administering a pharmaceutical composition in a therapeutically effective amount to a mammal in need thereof, said pharmaceutical composition comprising a herbal extract from a mixture of 3.5:1 *Dioscorea* Rhizoma:*Dioscorea nipponica* (w/w).

The dosage of the pharmaceutical composition comprising a herbal extract of a mixture of 3.5:1 *Dioscorea* Rhizoma:*Dioscorea nipponica* (w/w) may vary depending on various factors including the age, sex, weight, and health state of patients, diet, the time of administration, the route of administration, the rate of excretion, and the like. Typically, the pharmaceutical composition of the present invention may be administered may be administered in a single dose or in multiple doses per day, at a daily dosage ranging from 0.01 to 10 g/kg and preferably from 1 to 5 g/kg. However, it should be understood to those skilled in the art that the dosage does, in no way, limit the present invention.

The pharmaceutical composition comprising a herbal extract from a mixture of 3.5:1 *Dioscorea* Rhizoma:*Dioscorea nipponica* (w/w) in accordance with the present invention may be administered via various routes to mammals such as rats, mice, livestock, humans, etc. All routes of administration may be expected, for example, the pharmaceutical composition may be administered orally, intrarectally, intravenously, intramuscularly, subcutaneously, intrauterinely, intradurally or intracerebrovascularly.

Being almost free of toxicity and side effects, the herbal extract from a mixture of 3.5:1 *Dioscorea* Rhizoma:*Dioscorea nipponica* (w/w) can be safely ingested over a long period of time for the purpose of preventing diabetic neuropathy.

In the present invention, in vivo tests were performed to examine the ability of the herbal extract from a mixture of 3.5:1 *Dioscorea* Rhizoma:*Dioscorea nipponica* (w 1w) to raise the level of nerve growth factor in vivo and to alleviate symptoms of diabetic peripheral neuropathy. Data from animal models which were respectively healthy and suffered from diabetic neuropathy exhibited that the extract from the herb mixture of the specific ratio in accordance with the present invention had therapeutically synergistic effects compared to the extracts from herbs alone or herb mixtures of other weight ratios.

Contemplated in accordance with still another aspect thereof, the present invention is a health functional food for the prevention and amelioration of diabetic neuropathy, comprising a herbal extract from a mixture of 3.5:1 *Dioscorea* Rhizoma:*Dioscorea nipponica* (w/w) and a sitologically acceptable food additive.

As used herein, the term "health functional food" is intended to include those defined in the "2002 Law for health functional foods," such as health foods found in the list stipulating health functional food materials or ingredients verified for functionality and safety for humans according to KFDA Notice No. 2004-12 of the Korean Food and Drug Administration.

More particularly, the present invention provides a health functional food for the prevention and amelioration of diabetic neuropathy, comprising a herb extract from a mixture of 3.5:1 *Dioscorea* Rhizoma:*Dioscorea nipponica*, and a sitologically acceptable food additive.

The composition comprising a herb extract from a mixture of 3.5:1 *Dioscorea* Rhizoma:*Dioscorea nipponica* in accordance with the present invention can be applied to drugs, food and drink for alleviating symptoms of diabetic neuropathy. For example, the foods to which the herb extract of the present invention can be added include beverages, gum, teas, vitamin complexes, and food aids. For use in drugs, the herb extract may be in the form of pills, powders, granules, tablets, capsules or liquids.

When applied to solid foods, the herb extract of the present invention may be used in an amount of from 0.1 to 15% by weight based on the total weight of the food, and preferably in an amount of from 0.2 to 10% by weight. In a liquid form of health, the herb extract of the present invention may range in amount from 0.1 to 30 g per 100 mL of the liquid and preferably from 0.2 to 5 g.

Except for the specific ratio given to the indispensable herb ingredients, no particular limitations are imparted to the liquid health composition. Like typical beverages, the liquid health composition may further comprise various flavoring agents, natural carbohydrates, or other additives.

Preferable examples of the natural carbohydrates include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. The flavoring agents useful in the present invention may be natural (thaumatin, *stevia* extract (e.g., rebaudioside A, glycyrrhizin), or synthetic (saccharin, aspartame). Natural carbohydrates may be used in an amount of from about 1 to 20 g per 100 mL of the liquid health composition, and preferably in an amount of from about 5 to 12 g.

In addition, the composition of the present invention may contain various nutrients, vitamins, minerals (electrolytes), synthetic and/or natural flavoring agents, colorants, fillers (cheese, chocolate, etc.), pectic acid and its salts, alginic acid and its salts, organic acids, protective colloidal thickeners, pH modifiers, stabilizers, preservatives, glycerin, alcohols, and carbonating agents for carbonate beverages. For use in natural fruit juice, fruit juice beverages or vegetable beverages, the composition of the present invention may further contain fruit flesh. These additives may be used alone or in combination. Typical, but unimportant, amounts of the additives are on the order of from 0 to 20 parts by weight per 100 parts by weight of the composition.

Advantageous Effects of Invention

As described hitherto, the herb extract from a mixture of 3.5:1 *Dioscorea* Rhizoma:*Dioscorea nipponica* (w/w) in accordance with the present invention exhibits significantly higher, synergistic effects in terms of the elevation of in vivo level of nerve growth factor (NGF), the growth of neurites, and cognitive ability than those of extracts from *Dioscorea* Rhizoma or *Dioscorea nipponica* alone or a mixture of *Dioscorea* Rhizoma and *Dioscorea nipponica* in other weight ratios, and thus can be used in pharmaceutical compositions and health functional foods for the prevention and treatment of diabetic peripheral neuropathy.

MODE FOR THE INVENTION

Figure 1:
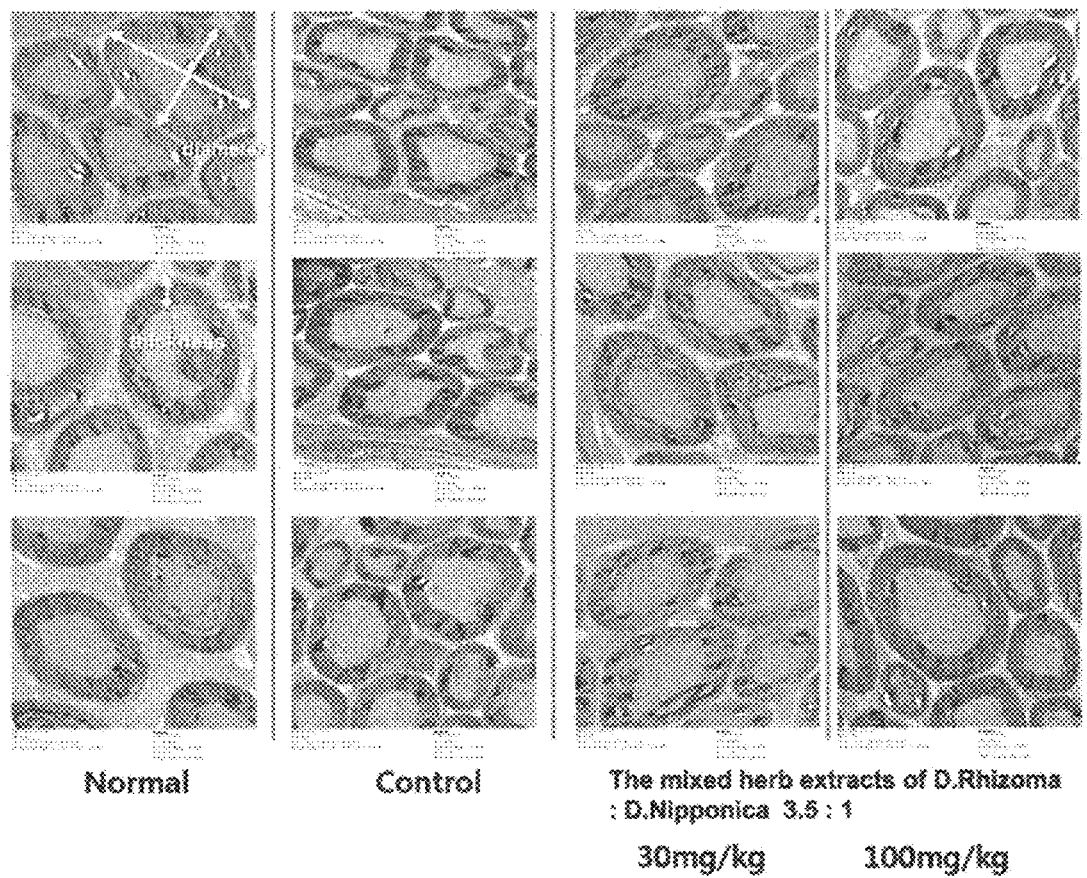
FIG. 1 is of electron photographs showing the effect of the extract of Example 1 on the sciatic nerve of type 1 diabetes mice.
Figure 2:
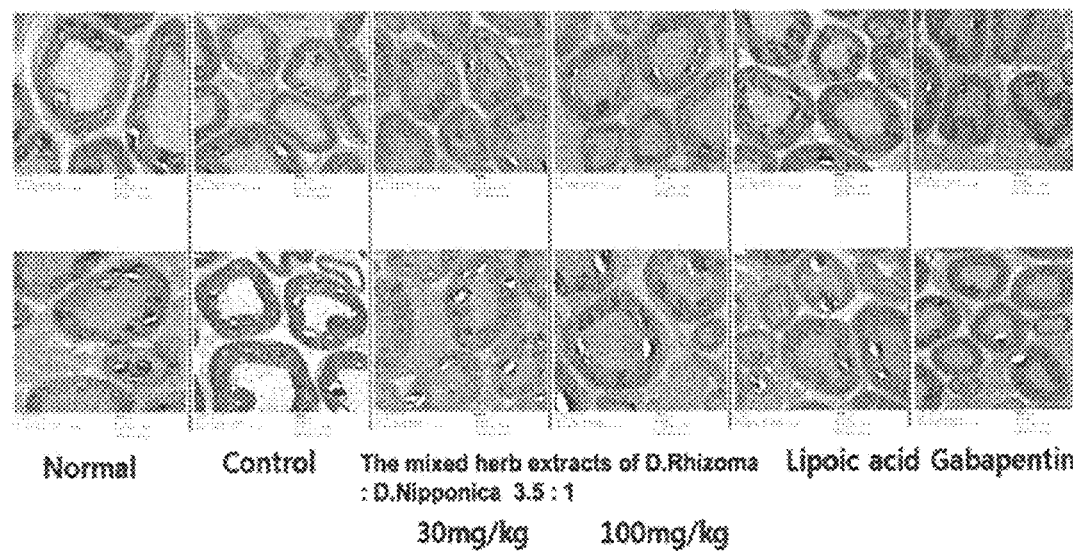
FIG. 2 is of electron photographs showing the effect of the extract of Example 1 on the sciatic nerve of type 1 diabetes rats.

A better understanding of the present invention may be obtained through the following examples which are set forth to illustrate, but are not to be construed as limiting the present invention.

Example 1

Preparation of Extract from Mixture of *Dioscorea* Rhizoma and *Dioscorea nipponica*

*Dioscorea* Rhizoma and *Dioscorea nipponica*, both in a dry condition, were purchased from a herb medicine shop in Kyoungdong market, Korea. After impurities were removed therefrom, the herbs were chopped with a cutter and mixed at a weight ratio of 3.5:1 *Dioscorea* Rhizoma:*Dioscorea nipponica*. To 2 kg of the mixture was added 10 L of a 50% ethanol solution, followed by incubation at room temperature for 48 hours with stirring. The herb mixture was removed by filtration, and the filtrate was concentrated in a vacuum and freeze dried to afford a mixed herb extract (crude extract) (see Table 1).

TABLE 1

Yield of Inventive Combined Herbal Extract

| Ex. | Amount of Material | | Solvent | Amount of Solvent | Wash | Extract'n Temp. | Time of Extract'n | Crude Extract (g) | Yield (%) |
| --- | --- | --- | --- | --- | --- | --- | --- | --- | --- |
| | D. Rhizoma | D. nipponica | | | | | | | |
| Ex. 1 | 1.55 kg | 0.45 kg | 50% EtOH | 10 L | 1 L | Room Temp. | 2 days | 212.85 | 10.64 |

Comparative Example 1

Preparation of *Dioscorea* Rhizoma Extract

A *Dioscorea* Rhizoma extract (crude extract) was prepared in the same manner as in Example 1, with the exception that 2 kg of *Dioscorea* Rhizoma was used instead of 2 kg of the mixture (see Table 2).

Comparative Example 2

Preparation of *Dioscorea nipponica* Extract

A *Dioscorea nipponica* extract (crude extract) was prepared in the same manner as in Example 1 with the exception that 2 kg of *Dioscorea nipponica* was used instead of 2 kg of the mixture (see Table 2).

TABLE 2

Yield of Respective Extracts from D Rhizoma and *D. Nipponica*

| # of C. Ex. | Amount of Material | | Solvent | Amount Of Solvent | Wash | Extract'n Temp. | Time of Extract'n | Crude Extract (g) | Yield (%) |
| --- | --- | --- | --- | --- | --- | --- | --- | --- | --- |
| | D. Rhizoma | D. nipponica | | | | | | | |
| 1 | 2 kg | — | 50% EtOH | 10 L | 1 L | Room Temp. | 2 days | 253.8 | 12.69 |
| 2 | — | 2 kg | 50% EtOH | 10 L | 1 L | Room Temp. | 2 days | 160.0 | 8.00 |

Comparative Example 3 to 10

Preparation of Extracts from Mixtures of *Dioscorea* Rhizoma and *Dioscorea nipponica*

The same herbs *Dioscorea* Rhizoma and *Dioscorea nipponica* as used in Example 1 were used. *Dioscorea* Rhizoma and *Dioscorea nipponica* were chopped with a cutter and mixed at the weight ratios listed in Table 3. To 2 kg of each of the mixtures was added 10 L of a 50% ethanol solution, followed by incubation at room temperature for 48 hours with stirring. The herb mixtures were removed by filtration, and the filtrate was concentrated in a vacuum and freeze dried to afford mixed herb extracts (crude extracts).

divided into groups according to weight. The extracts prepared in the above Examples were orally administered in predetermined amounts to the mice, with Gabapentin used as a positive control at a dose of 100 mg/kg, 16 hours after which blood was sampled from the mice. They were then sacrificed to obtain the sciatic nerve and the salivary glands.

After the blood samples were centrifuged at 10,000 rpm for 10 min, the levels of nerve growth factor in the plasma thus separated were measured by ELISA (ABS 450 nm). The sciatic nerve and the salivary glands were weighed and a solution containing 100 mM Tris-HCl, 1M NaCl, 2% BSA, 4 mM EDTA, 2.0% Trtion®X-100, 0.02% sodium azide. 0.1 mg/ml pepstatin A, 5 mg/ml aprotonin, 0.5 mg/ml antipain,

TABLE 3

Yield of Combined Extract of Mixture of D. Rhizoma and D. Nipponica

| # of C. Ex. | Amount of Material | | Solvent | | Washing | Extract'n Temp. | Time of Extract'n | Crude Extract (g) | Yield (%) |
|---|---|---|---|---|---|---|---|---|---|
| | D. Rhizoma | D. nipponica | Kind | Amount | | | | | |
| 3 | 1 | 1 | 50% EtOH | 10 L | 1 L | Room Temp. | 2 days | 179.05 | 8.95 |
| 4 | 1.33 | 0.67 | 50% EtOH | 10 L | 1 L | Room Temp. | 2 days | 135.96 | 6.80 |
| 5 | 1.67 | 0.33 | 50% EtOH | 10 L | 1 L | Room Temp. | 2 days | 160.07 | 8.00 |
| 6 | 1.82 | 0.18 | 50% EtOH | 10 L | 1 L | Room Temp. | 2 days | 138.75 | 6.93 |
| 7 | 0.67 | 1.33 | 50% EtOH | 10 L | 1 L | Room Temp. | 2 days | 153.56 | 7.68 |
| 8 | 0.45 | 1.55 | 50% EtOH | 10 L | 1 L | Room Temp. | 2 days | 139.15 | 6.96 |
| 9 | 0.33 | 1.67 | 50% EtOH | 10 L | 1 L | Room Temp. | 2 days | 181.06 | 9.05 |
| 10 | 0.18 | 1.82 | 50% EtOH | 10 L | 1 L | Room Temp. | 2 days | 146.43 | 7.32 |

Test Example 1

Test for In Vivo Level of Nerve Growth Factor in Normal Mouse Model

Ability of the crude extract with 50% ethanol in Example 1 to induce the secretion of nerve growth factor in vivo was evaluated (O. Arrieta and J. Sotelo et al., Retinoic acid increases tissue and plasma contents of nerve growth factor and prevents neuropathy in diabetic mice. European Journal of Clinical Investigation (2005) 35).

Male ICR mice, each weighing 25-30 g, were acclimated for 1 week at 22-24° C. at a relative humidity of 60-80% while being fed with water and a standard diet. They were 167 mg/ml benzamidine, and 5.2 mg/ml PMSF was added in amounts proportional to the weights, followed by homogenization. The homogenates were incubated for 15 min with 1N HCl in an amount of 1 μl/50 μl for oxidization and neutralized with 1N NaOH in an amount of 1 μl/50 μl. Centrifugation was performed at 10,000 rpm for 10 min to obtain supernatants. Like plasma, the sciatic nerve and the salivary glands were quantitatively analyzed for the level of nerve growth factor.

Data are summarized in Table 4 for plasma NGF levels, in Table 5 for sciatic NGF levels, and in Table 6 for salivary gland NGF levels.

TABLE 4

NGF Level in Plasma

| Group | Amount of material (kg) | | Weight ratio of D. Rhizoma:D. nipponica | Dose (mg/kg) | NGF Level in Plasma (pg/ml) |
|---|---|---|---|---|---|
| | D. Rhizoma | D. nipponica | | | |
| control | | | | | 601.5 |
| Ex. 1 | 1.55 | 0.45 | 3.5:1 | 100 | 1106.9 |
| C. Ex. 1 | 2 | — | — | 100 | 606.2 |
| C. Ex. 2 | — | 2 | — | 100 | 602.1 |
| C. Ex. 3 | 1 | 1 | 1:1 | 100 | 663.6 |
| C. Ex. 4 | 1.33 | 0.67 | 1:2 | 100 | 689.9 |
| C. Ex. 5 | 1.67 | 0.33 | 5:1 | 100 | 725.6 |
| C. Ex. 6 | 1.82 | 0.18 | 10:1 | 100 | 696.8 |
| C. Ex. 7 | 0.67 | 1.33 | 1:2 | 100 | 607.0 |
| C. Ex. 8 | 0.45 | 1.55 | 1:3.5 | 100 | 656.0 |
| C. Ex. 9 | 0.33 | 1.67 | 1:5 | 100 | 642.6 |

TABLE 4-continued

NGF Level in Plasma

| Group | Amount of material (kg) D. Rhizoma | Amount of material (kg) D. nipponica | Weight ratio of D. Rhizoma:D. nipponica | Dose (mg/kg) | NGF Level in Plasma (pg/ml) |
|---|---|---|---|---|---|
| C. Ex. 10 | 0.18 | 1.82 | 1:10 | 100 | 640.7 |
| Gabapentin | | | | 100 | 610.4 |

When administered at the same dosage, as can be seen in Table 4, the *Dioscorea Rhizoma* extract of Comparative Example 1, the *Dioscorea nipponica* extract of Comparative Example 2, and the extracts from mixtures of *Dioscorea Rhizoma* and *Dioscorea nipponica* of Comparative Examples 3 to 10 were observed to induce the secretion of nerve growth factor in plasma to a degree similar to that of the control. In contrast, the extract of Example 1 increased the plasma NGF level over that obtained by the *Dioscorea Rhizoma* extract, the *Dioscorea nipponica* extract, or the extracts from mixtures of *Dioscorea* Rhizoma and *Dioscorea nipponica* at other weight ratios.

Increasing the level of nerve growth factor in plasma, a path through which nerve growth factor moves toward targets, indicates promoting the secretion of nerve growth factor. Thus, the extract from a mixture of 3.5:1 *Dioscorea* Rhizoma:*Dioscorea nipponica* (w/w) in accordance with the present invention further promotes the secretion of nerve growth factor to significantly raise the level of NGF in vivo, compared to the extracts from *Dioscorea* Rhizoma alone, *Dioscorea nipponica* alone or from mixtures of *Dioscorea* Rhizoma and *Dioscorea nipponica* at other weight ratios.

TABLE 5

NGF Level in Sciatic Nerve

| Group | Amount of material (kg) D. Rhizoma | Amount of material (kg) D. nipponica | Weight ratio of D. Rhizoma:D. nipponica | Dose (mg/kg) | NGF Level in Sciatic Nerve (pg/mg) |
|---|---|---|---|---|---|
| control | | | | | 3.3 |
| Ex. 1 | 1.55 | 0.45 | 3.5:1 | 100 | 7.5 |
| C. Ex. 1 | 2 | — | — | 100 | 3.8 |
| C. Ex. 2 | — | 2 | — | 100 | 3.6 |
| C. Ex. 3 | 1 | 1 | 1:1 | 100 | 4.6 |
| C. Ex. 4 | 1.33 | 0.67 | 1:2 | 100 | 4.1 |
| C. Ex. 5 | 1.67 | 0.33 | 5:1 | 100 | 4.0 |
| C. Ex. 6 | 1.82 | 0.18 | 10:1 | 100 | 3.2 |
| C. Ex. 7 | 0.67 | 1.33 | 1:2 | 100 | 5.1 |
| C. Ex. 8 | 0.45 | 1.55 | 1:3.5 | 100 | 4.6 |
| C. Ex. 9 | 0.33 | 1.67 | 1:5 | 100 | 4.0 |
| C. Ex. 10 | 0.18 | 1.82 | 1:10 | 100 | 4.9 |
| α-Lipoic acid | | | | 50 | 5.0 |
| Gabapentin | | | | 100 | 4.2 |

Observations showed that, when administered at the same dosage, as can be seen in Table 5, the *Dioscorea* Rhizoma extract of Comparative Example 1, the *Dioscorea nipponica* extract of Comparative Example 2, and the extracts from mixtures of *Dioscorea Rhizoma* and *Dioscorea nipponica* of Comparative Examples 3 to 10 secreted nerve growth factor in the sciatic nerve to a degree similar to that of the control. In contrast, the extract of Example 1 increased the sciatic nerve NGF level over that obtained by the *Dioscorea* Rhizoma extract, the *Dioscorea nipponica* extract, or the extracts from mixtures of *Dioscorea* Rhizoma and *Dioscorea nipponica* at other weight ratios.

Accordingly, the extract from a mixture of 3.5:1 *Dioscorea* Rhizoma:*Dioscorea nipponica* in accordance with the present invention can induce the secretion of NGF into the blood, which results in a significant increase in the level of NGF in the sciatic nerve, the target tissue.

TABLE 6

NGF Level in Salivary Gland

| Group | Amount of material(kg) D. Rhizoma | Amount of material(kg) D. nipponica | Weight ratio of D. Rhizoma:D. nipponica | Dose (mg/kg) | NGF Level in Salivary Gland (ng/mg) |
|---|---|---|---|---|---|
| control | | | | | 166.1 |
| Ex. 1 | 1.55 | 0.45 | 3.5:1 | 100 | 221.7 |
| C. Ex. 1 | 2 | — | — | 100 | 171.6 |
| C. Ex. 2 | — | 2 | — | 100 | 170.1 |
| C. Ex. 3 | 1 | 1 | 1:1 | 100 | 206.2 |
| C. Ex. 4 | 1.33 | 0.67 | 2:1 | 100 | 193.3 |
| C. Ex. 5 | 1.67 | 0.33 | 5:1 | 100 | 177.4 |

TABLE 6-continued

NGF Level in Salivary Gland

| Group | Amount of material(kg) D. Rhizoma | Amount of material(kg) D. nipponica | Weight ratio of D. Rhizoma:D. nipponica | Dose (mg/kg) | NGF Level in Salivary Gland (ng/mg) |
|---|---|---|---|---|---|
| C. Ex. 6 | 1.82 | 0.18 | 10:1 | 100 | 202.5 |
| C. Ex. 7 | 0.67 | 1.33 | 1:2 | 100 | 173.4 |
| C. Ex. 8 | 0.45 | 1.55 | 1:3.5 | 100 | 200.2 |

TABLE 6-continued

NGF Level in Salivary Gland

| Group | Amount of material(kg) D. Rhizoma | Amount of material(kg) D. nipponica | Weight ratio of D. Rhizoma:D. nipponica | Dose (mg/kg) | NGF Level in Salivary Gland (ng/mg) |
|---|---|---|---|---|---|
| C. Ex. 9 | 0.33 | 1.67 | 1:5 | 100 | 181.2 |
| C. Ex. 10 | 0.18 | 1.82 | 1:10 | 100 | 188.1 |
| α-Lipoic acid | | | | 50 | 164.4 |
| Gabapentin | | | | 100 | 193.1 |

As is apparent from the data of Table 6, when administered at the same dosage, the *Dioscorea* Rhizoma extract of Comparative Example 1 and the *Dioscorea nipponica* extract of Comparative Example 2 increased the level of NGF in the salivary glands by 2~3% only, compared to the control while the extracts from mixtures of *Dioscorea* Rhizoma and *Dioscorea nipponica* of Comparative Examples 3 to 10 induced the secretion of NGF in the salivary glands to degrees similar to or less than those obtained by the positive control gabapentin. In contrast, the level of NGF in the salivary glands was 33.5% increased by the extract of Example 1. That is, the extract of the present invention allowed for a significant increase in the level of NGF in the salivary gland, compared to the extracts from *Dioscorea* Rhizoma alone, *Dioscorea nipponica* alone or mixtures of *Dioscorea* Rhizoma and *Dioscorea nipponica* at other weight ratios. Increasing the level of NGF in the salivary gland, which functions as a source of NGF, means promoting the synthesis of NGF.

Consequently, the herb extract of a mixture of 3.5:1 *Dioscorea* Rhizoma:*Dioscorea nipponica* (w/w) can significantly raise the level of NGF in vivo.

Hence, thanks to its ability to significantly raise the level of NGF in vivo, the herb extract of a mixture of 3.5:1 *Dioscorea* Rhizoma:*Dioscorea nipponica* (w/w) in accordance with the present invention can be applied to a pharmaceutical composition or a health functional food for the prevention and treatment of diabetic peripheral neuropathy.

Test Example 2

Test for Effects on Pain, NGF Secretion, and Neurodegeneration in SD Male Rats with Streptozotocin-Induced Type 1 Diabetes The herb extract of a mixture of 3.5:1 *Dioscorea* Rhizoma:*Dioscorea nipponica*, prepared in Example 1, and the extracts of Comparative Examples 1 to 10 were evaluated for effects on pain, in vivo NGF level and neurodegeneration in SD male rats with type 1 diabetes.

SD male rats, each weighing 220~250 g, were acclimated for one week at 22-24° C. at a relative humidity of 60-80% with standard diet and water fed thereto. Thereafter, a solution of streptozotocin in saline was intravenously administered once at a dose of 50 mg/kg to the rats to induce type 1 diabetes. Four weeks after the induction of diabetes, rats were divided into groups according to blood sugar level. The extracts prepared in the above Examples were orally administered once a day for 8 weeks at predetermined doses to the rats, while α-lipoic acid and Gabapentin were used as positive controls at doses of 50 mg/kg and 100 mg/kg, respectively. Then, they were sacrificed to obtain the sciatic nerve and the salivary glands. The sciatic nerve and the salivary glands were processed in the same manner as in Test Example 1 and measured for NGF level by ELISA. The results are summarized in Table 7, below.

The ability of the extracts to alleviate the pain caused by diabetic neuropathy was examined. In this regard, rats with streptozotocin-induced diabetes were separated and orally administered with the extracts at a predetermined dose once a day for 14 weeks, with α-lipoic acid 50 mg/kg and Gabapentin 100 mg/kg serving as positive controls. A Randall-Sellito test was performed to measure a threshold response to pressure on a paw. The latent time taken to respond to a thermal pain was measured using a tail-flick test. The results are summarized in Table 8. In order to evaluate the neurodegeneration which had progressed with the onset of diabetic neuropathy, the sciatic nerve taken from the rats of each group was fixed with formalin and observed under an electron microscope to measure the size and thickness of the myelin sheath, and the results are summarized in Table 9.

TABLE 7

NGF Level in Sciatic Nerve of Type 2 Diabetes Rat Model (SD Male Rat)

| Group | Amount of material(kg) D. Rhizoma | Amount of material(kg) D. nipponica | Weight ratio of D. Rhizoma:D. nipponica | Dose (mg/kg) | NGF Level Sciatic Nerve (pg/mg) | NGF Level Salivary Gland (ng/mg) |
|---|---|---|---|---|---|---|
| Normal | | | | | 25.5 | 4.1 |
| control | | | | | 11.9 | 2.1 |
| Ex. 1 | 1.55 | 0.45 | 3.5:1 | 100 | 35.4 | 3.8 |
| C. Ex. 1 | 2 | — | — | 100 | 13.1 | 2.0 |
| C. Ex. 2 | — | 2 | — | 100 | 12.7 | 1.7 |
| C. Ex. 3 | 1 | 1 | 1:1 | 100 | 19.2 | 1.9 |
| C. Ex. 4 | 1.33 | 0.67 | 2:1 | 100 | 27.9 | 2.4 |
| C. Ex. 5 | 1.67 | 0.33 | 5:1 | 100 | 25.1 | 2.9 |
| C. Ex. 6 | 1.82 | 0.18 | 10:1 | 100 | 24.6 | 2.8 |
| C. Ex. 7 | 0.67 | 1.33 | 1:2 | 100 | 19.1 | 3.3 |
| C. Ex. 8 | 0.45 | 1.55 | 1:3.5 | 100 | 19.8 | 2.9 |
| C. Ex. 9 | 0.33 | 1.67 | 1:5 | 100 | 20.9 | 2.9 |
| C. Ex. 10 | 0.18 | 1.82 | 1:10 | 100 | 16.4 | 2.5 |
| α-Lipoic acid | | | | 50 | 13.8 | 2.8 |
| Gabapentin | | | | 100 | 14.9 | 2.4 |

When administered at the same dosage, as can be seen in Table 7, the extract of Example 1 significantly increased the level of NGF in both the sciatic nerve and the salivary gland, compared to the *Dioscorea* Rhizoma extract of Comparative Example 1, the *Dioscorea nipponica* extract of Comparative Example 2, or the extracts from mixtures of *Dioscorea* Rhizoma and *Dioscorea nipponica* of Comparative Examples 3 to 10

Thus, the herb extract of a mixture of 3.5:1 *Dioscorea* Rhizoma:*Dioscorea nipponica* was proven to induce a significant increase of NGF in the target tissues (sciatic nerve, salivary gland) even in animals with type 1 diabetes.

TABLE 8

Assay for Pain Response in Type 1 Diabetes Rat Model (SD Male Rat)

| | Amount of material(kg) | | Weight ratio of D. Rhizoma:D. nipponica | Dose (mg/kg) | Pressure Pain Threshold (g) | Latent Time to Pain Reaction (sec) |
|---|---|---|---|---|---|---|
| | D. Rhizoma | D. nipponica | | | | |
| Normal | | | | | 270.0 | 9.9 |
| control | | | | | 128.8 | 5.4 |
| Ex. 1 | 1.55 | 0.45 | 3.5:1 | 100 | 191.7 | 11.4 |
| C. Ex. 1 | 2 | — | — | 100 | 130.1 | 6.3 |
| C. Ex. 2 | — | 2 | — | 100 | 129.8 | 6.7 |
| C. Ex. 3 | 1 | 1 | 1:1 | 100 | 169.0 | 8.0 |
| C. Ex. 4 | 1.33 | 0.67 | 2:1 | 100 | 163.7 | 7.8 |
| C. Ex. 5 | 1.67 | 0.33 | 5:1 | 100 | 138.0 | 7.4 |
| C. Ex. 6 | 1.82 | 0.18 | 10:1 | 100 | 150.0 | 7.2 |
| C. Ex. 7 | 0.67 | 1.33 | 1:2 | 100 | 153.5 | 7.9 |
| C. Ex. 8 | 0.45 | 1.55 | 1:3.5 | 100 | 157.0 | 7.6 |
| C. Ex. 9 | 0.33 | 1.67 | 1:5 | 100 | 157.6 | 7.1 |
| C. Ex. 10 | 0.18 | 1.82 | 1:10 | 100 | 129.2 | 7.5 |
| α-Lipoic acid | | | | 50 | 150.0 | 7.4 |
| Gabapentin | | | | 100 | 137.7 | 7.7 |

As can be seen in Table 8, when administered at the same dose, the extract of Example 1 significantly increased both the pressure pain threshold and the latent time to pressure response, compared to the *Dioscorea* Rhizoma extract of Comparative Example 1, the *Dioscorea nipponica* extract of Comparative Example 2, or the extracts from mixtures of *Dioscorea* Rhizoma and *Dioscorea nipponica* of Comparative Examples 3 to 10.

An increase in threshold to mechanical stimuli delineates an increase in threshold to pain. In the tail flick test, an increase in latent time to pain response corresponds to an increase in threshold to thermal stimuli, indicating the alleviation of pain.

Hence, the herb extract of a mixture of 3.5:1 *Dioscorea* Rhizoma:*Dioscorea nipponica* in accordance with the present invention exhibited a significant alleviative effect on pain, a symptom of diabetic peripheral neuropathy.

TABLE 9

Assay for Neurodegeneration in Type 1 Diabetes Rat Model (SD Male Rat)

| | Dose (mg/kg) | Neurodegeneration | |
|---|---|---|---|
| | | Size of Myelin sheath (μm) | Thickness of Myelin sheath (μm) |
| Normal | | 15.3 | 3.2 |
| control | | 9.3 | 2.5 |
| Ex. 1 | 30 | 13.6 | 3.2 |
| | 100 | 13.8 | 2.9 |
| α-Lipoic acid | 50 | 11.2 | 2.6 |
| Gabapentin | 100 | 10.4 | 2.2 |

As is apparent from the data of Table 9, both size and thickness of the myelin sheath of the control became smaller, indicating the damage or degeneration of the sciatic nerve due to diabetic neuropathy. When administered with the extract of Example 1, both size and thickness of the myelin sheath of the rats were observed to become bigger.

Therefore, the extract of the present invention can ameliorate neurodegeneration, giving rise to nerve regeneration in target organs even in a histological aspect.

Consequently, the herb extract in accordance with the present invention can be applied to a pharmaceutical composition which can bring about a significant synergistic effect on the prevention and treatment of diabetic peripheral neuropathy in subjects with type 1 diabetes.

Test Example 3

Test for Effects on Pain, NGF Secretion, and Neurodegeneration in ICR Male Mice with Streptozotocin-Induced Type 1 Diabetes The herb extract of a mixture of 3.5:1 *Dioscorea* Rhizoma:*Dioscorea nipponica*, prepared in Example 1, was evaluated for effects on pain, in vivo NGF level and neurodegeneration in ICR male mice with type 1 diabetes.

ICR male mice, each weighing 25~30 g, were acclimated for one week at 22-24° C. at a relative humidity of 60-80%, with a standard diet and water fed thereto. Thereafter, a solution of streptozotocin in saline was intravenously administered once at a dose of 200 mg/kg to the mice to induce type 1 diabetes. Four weeks after the induction of diabetes, rats were divided into groups according to blood sugar level. The extracts prepared in the above Examples were orally administered once a day for 14 weeks at predetermined doses to the mice, while α-lipoic acid and Gabapentin were used as positive controls at a dose of 50 mg/kg and 100 mg/kg, respectively. Mice in each group were placed on a 58° C. hot plate, and examined for hyperalgesia to heat stimulus by measuring the latent time it took for the mice to feel a heat pain on their foot soles and jump. The results are summarized in Table 10.

Then, the mice were sacrificed to obtain the sciatic nerve and the salivary glands therefrom. The sciatic nerve and the salivary glands were processed in the same manner as in Test Example 1 and measured for NGF level by ELISA. The results are summarized in Table 11, below.

In order to evaluate the neurodegeneration which had progressed with the onset of diabetic neuropathy, the sciatic nerve taken from the mice of each group was fixed with formalin and observed under an electron microscope to measure the size and thickness of the myelin sheath, and the results are summarized in Table 12.

TABLE 10

Assay for Pain Response in Type 1 Diabetes Mouse Model (ICR Male Mouse)

| Group | Dose (mg/kg) | Latent Time to Pain Response on 58° C. Hot Plate (sec) |
|---|---|---|
| Normal | | 55.3 |
| control | | 25.2 |
| Ex. 1 | 100 | 45.9 |
| C. Ex. 1 | 100 | 26.6 |
| C. Ex. 2 | 100 | 25.7 |
| C. Ex. 3 | 100 | 35.6 |
| C. Ex. 4 | 100 | 25.3 |
| C. Ex. 5 | 100 | 26.0 |
| C. Ex. 6 | 100 | 35.0 |
| C. Ex. 7 | 100 | 32.2 |
| C. Ex. 8 | 100 | 33.0 |
| C. Ex. 9 | 100 | 26.8 |
| C. Ex. 10 | 100 | 36.1 |
| α-Lipoic acid | 50 | 31.1 |
| Gabapentin | 100 | 33.0 |

An increase in latent time to pain response on the hot plate reflects an increase in pain threshold to thermal stimuli, indicating a reduction in pain. As can be seen in Table 10, the extract of Example 1 significantly increased the latent time to pain response on a hot plate, compared to the *Dioscorea* Rhizoma extract of Comparative Example 1, the *Dioscorea nipponica* extract of Comparative Example 2, or the extracts from mixtures of *Dioscorea* Rhizoma and *Dioscorea nipponica* of Comparative Examples 3 to 10, demonstrating that the herb composition of the present invention has a significant alleviative effect on pain, a symptom of diabetic peripheral neuropathy.

TABLE 11

NGF Levels in Sciatic Nerve and Salivary Gland in Type 1 Diabetes Mouse Model (ICR Male Mouse)

| | | NGF Level | |
|---|---|---|---|
| Group | Dose (mg/kg) | Sciatic Nerve (pg/mg) | Salivary Gland (ng/mg) |
| Normal | | 9.7 | 226.1 |
| control | | 3.9 | 101.8 |
| Ex. 1 | 100 | 9.2 | 169.6 |
| C. Ex. 1 | 100 | 4.1 | 107.2 |
| C. Ex. 2 | 100 | 3.9 | 104.3 |
| C. Ex. 3 | 100 | 6.2 | 118.7 |
| C. Ex. 4 | 100 | 4.8 | 115.8 |
| C. Ex. 5 | 100 | 4.0 | 121.0 |
| C. Ex. 6 | 100 | 3.6 | 114.3 |
| C. Ex. 7 | 100 | 6.2 | 122.7 |
| C. Ex. 8 | 100 | 4.8 | 104.7 |
| C. Ex. 9 | 100 | 4.1 | 104.7 |
| C. Ex. 10 | 100 | 3.5 | 120.4 |
| α-Lipoic acid | 50 | 5.7 | 118.7 |
| Gabapentin | 100 | 5.5 | 117.1 |

As can be seen in Table 11, the extract of Example 1 significantly increased the level of NGF in both the sciatic nerve and the salivary gland, compared to the *Dioscorea Rhizoma* extract of Comparative Example 1, the *Dioscorea nipponica* extract of Comparative Example 2, or the extracts from mixtures of *Dioscorea* Rhizoma and *Dioscorea nipponica* of Comparative Examples 3 to 10.

Thus, the herb extract of a mixture of 3.5:1 *Dioscorea* Rhizoma:*Dioscorea nipponica* is proven to induce a significant increase of NGF in the target organs (sciatic nerve, salivary gland) in ICR male mice with type 1 diabetes as well as SD male rats with type 1 diabetes.

TABLE 12

Assay for Neurodegeneration in Type 1 Diabetes Mouse Model (ICR Male Mouse)

| | | Neurodegeneration | |
|---|---|---|---|
| Group | Dose (mg/kg) | Size of Myelin sheath (μm) | Thickness of Myelin sheath (μm) |
| Normal | | 14.3 | 3.4 |
| control | | 9.1 | 2.0 |
| Ex. 1 | 30 | 13.7 | 2.9 |
| | 100 | 12.9 | 2.6 |

As is apparent from the data of Table 12, the myelin sheath of the control was decreased in both size and thickness, indicating the damage or degeneration of the sciatic nerve due to diabetic neuropathy. When administered with the extract of Example 1, mice were observed to have a myelin sheath which was increased in both size and thickness.

Therefore, the extract of the present invention can ameliorate neurodegeneration in ICR mice with type 1 diabetes as well as SD rats with type 1 diabetes, giving rise to nerve regeneration in target organs even in a histological aspect.

Consequently, the herb extract in accordance with the present invention can be applied to a pharmaceutical composition which can bring about a significant synergistic effect on the prevention and treatment of diabetic peripheral neuropathy in subjects with type 1 diabetes.

Test Example 4

Test for Effects on Pain and NGF Secretion in Male Mice with Type 2 Diabetes Induced Genetically (Db/Db Male Mice)

The herb extract of a mixture of 3.5:1 *Dioscorea* Rhizoma:*Dioscorea nipponica*, prepared in Example 1, was evaluated for effects on pain and in vivo NGF level in db/db male mice with type 2 diabetes.

db/db Male mice, each weighing 40~45 g, were acclimated for one week at 22-24° C. at a relative humidity of 60-80%, with a standard diet and water fed thereto. On the day of the 9th week after birth, the mice in which diabetes had been induced were selected. Four weeks later, mice suffering from type 2 diabetes were separated according to blood sugar level. The extracts prepared in the above Examples were orally administered once a day for 12 weeks at predetermined doses to the mice, while α-lipoic acid and Gabapentin were used as positive controls at a dose of 50 mg/kg and 100 mg/kg, respectively. Mice in each group were placed on a 58° C. hot plate, and examined for hyperalgesia to heat stimulus by measuring the latent time it took for the mice to feel a heat pain on their foot soles and jump. The results are summarized in Table 13.

Then, the mice were sacrificed to obtain the sciatic nerve therefrom. The sciatic nerve was processed in the same manner as in Test Example 1 and its NGF level was measured by ELISA. The results are summarized in Table 14, below.

TABLE 13

Assay for Pain Response in Type 2 Diabetes Mouse Model (db/db Male Mouse)

| Group | Dose (mg/kg) | Latent Time to Pain Response on 58° C. Hot Plate (sec) |
|---|---|---|
| control | | 12.7 |
| Ex. 1 | 100 | 28.0 |
| C. Ex. 1 | 100 | 15.1 |
| C. Ex. 2 | 100 | 14.9 |
| C. Ex. 3 | 100 | 21.3 |
| C. Ex. 4 | 100 | 21.0 |
| C. Ex. 5 | 100 | 20.5 |
| C. Ex. 6 | 100 | 19.3 |
| C. Ex. 7 | 100 | 22.3 |
| C. Ex. 8 | 100 | 17.6 |
| C. Ex. 9 | 100 | 17.6 |
| C. Ex. 10 | 100 | 16.8 |
| α-Lipoic acid | 50 | 15.4 |
| Gabapentin | 100 | 16.1 |

As can be seen in Table 13, the extract of Example 1 significantly increased the latent time to pain response on a hot plate, compared to the *Dioscorea* Rhizoma extract of Comparative Example 1, the *Dioscorea nipponica* extract of Comparative Example 2, or the extracts from mixtures of *Dioscorea* Rhizoma and *Dioscorea nipponica* of Comparative Examples 3 to 10, demonstrating that the herb composition of the present invention has a significant alleviative effect on pain, a symptom of diabetic peripheral neuropathy.

TABLE 14

NGF Level in Sciatic Nerve of Type 2 Diabetes Mouse Model (db/db Male Mouse)

| Group | Dose (mg/kg) | NGF Level in Sciatic Nerve (pg/mg) |
|---|---|---|
| control | | 6.2 |
| Ex. 1 | 100 | 11.6 |
| C. Ex. 1 | 100 | 6.5 |
| C. Ex. 2 | 100 | 6.3 |
| C. Ex. 3 | 100 | 8.4 |
| C. Ex. 4 | 100 | 8.3 |
| C. Ex. 5 | 100 | 7.8 |
| C. Ex. 6 | 100 | 6.9 |
| C. Ex. 7 | 100 | 8.1 |
| C. Ex. 8 | 100 | 7.0 |
| C. Ex. 9 | 100 | 7.1 |
| C. Ex. 10 | 100 | 7.3 |
| α-Lipoic acid | 50 | 7.6 |
| Gabapentin | 100 | 7.2 |

As can be seen in Table 14, the extract of Example 1 significantly increased the level of NGF in the sciatic nerve, compared to the *Dioscorea* Rhizoma extract of Comparative Example 1, the *Dioscorea nipponica* extract of Comparative Example 2, or the extracts from mixtures of *Dioscorea* Rhizoma and *Dioscorea nipponica* of Comparative Examples 3 to 10.

Thus, the herb extract of a mixture of 3.5:1 *Dioscorea* Rhizoma:*Dioscorea nipponica* is proven to induce a significant increase of NGF in the target organ even under the condition of type 2 diabetes.

Having the ability to significantly increase in vivo NGF levels, the herb extract in accordance with the present invention can be applied to a pharmaceutical composition which can bring about a significant synergistic effect on the prevention and treatment of diabetic peripheral neuropathy in subjects with type 1 or 2 diabetes.

Test Example 5

Test for Activity of Inducing Synthesis of NGF and Growth of Nerve Cells Using C6 Rat Glioma Cells and PC12 Nerve Cells The herb extract of a mixture of 3.5:1 *Dioscorea* Rhizoma:*Dioscorea nipponica* (w/w), prepared in Example 1, was examined for its ability to induce the synthesis of NGF in C6 rat glioma cells and the growth of PC12 rat nerve cells.

In order to evaluate the ability of the extract to induce the synthesis of NGF, C6 glioma cells were seeded at the same density per well into plates and incubated for 24 hours. The cells were washed with PBS, and cultured for 48 hours in fresh culture media supplemented with 50 μg/mL or 250 μg/mL herb extracts of Examples 1 or Comparative Examples 1 to 10. Then, the culture media were harvested and their NGF levels were quantitatively analyzed using ELISA. The results are summarized in Table 15.

For use in a test for ability to induce nerve cell growth, PC12 nerve cells were seeded at the same density per well into plates and incubated for 24 hours. The cells were washed with PBS and cultured for 48 hours in culture media supplemented with the herb extracts of Example 1 or Comparative Examples 1 to 10 or NGF. The growth of the cells was measured using MTS assay, and the results are summarized in Table 16.

TABLE 15

Promotive Effect on Synthesis of NGF

| Group | Dose (μg/ml) | NGF Level (% of control) |
|---|---|---|
| control | | 100 |
| Ex. 1 | 50 | 113 |
| | 250 | 149 |
| C. Ex. 1 | 50 | — |
| | 250 | 107 |

TABLE 15-continued

Promotive Effect on Synthesis of NGF

| Group | Dose (μg/ml) | NGF Level (% of control) |
|---|---|---|
| C. Ex. 2 | 50 | — |
|  | 250 | 103 |
| C. Ex. 3 | 50 | 108 |
|  | 250 | 110 |
| C. Ex. 4 | 50 | 102 |
|  | 250 | 105 |
| C. Ex. 5 | 50 | 101 |
|  | 250 | 110 |
| C. Ex. 6 | 50 | 105 |
|  | 250 | 111 |
| C. Ex. 7 | 50 | 102 |
|  | 250 | 122 |
| C. Ex. 8 | 50 | 107 |
|  | 250 | 128 |
| C. Ex. 9 | 50 | 104 |
|  | 250 | 119 |
| C. Ex. 10 | 50 | 101 |
|  | 250 | 123 |

As can be seen in Table 15, the extract of Example 1 significantly increased the level of NGF in the C6 cells, compared to the extract of Comparative Example 1 (from *Dioscorea* Rhizoma alone), the extract of Comparative Example 2 (from *Dioscorea nipponica* alone) or the extracts of Comparative Examples 3 to 10 (from mixtures of *Dioscorea* Rhizoma and *Dioscorea nipponica* at other weight ratios).

Thus, the herb extract of a mixture of 3.5:1 *Dioscorea* Rhizoma:*Dioscorea nipponica* is proven to maximally induce the synthesis of NGF.

TABLE 16

Proliferative Effect on Nerve Cells

| Group | Dose (μg/ml) | Proliferative Effect on Nerve Cell (% of control) |
|---|---|---|
| control |  | 100 |
| NGF | 2 (ng/ml) | 112 |
|  | 50 (ng/ml) | 118 |
| Ex. 1 | 1 | 111 |
|  | 30 | 117 |
| C. Ex. 1 | 1 | — |
|  | 30 | 101 |
| C. Ex. 2 | 1 | — |
|  | 30 | 100 |
| C. Ex. 3 | 1 | 101 |
|  | 30 | 105 |
| C. Ex. 4 | 1 | 98 |
|  | 30 | 103 |
| C. Ex. 5 | 1 | 100 |
|  | 30 | 101 |
| C. Ex. 6 | 1 | 99 |
|  | 30 | 102 |
| C. Ex. 7 | 50 | 104 |
|  | 250 | 106 |
| C. Ex. 8 | 50 | 100 |
|  | 250 | 103 |
| C. Ex. 9 | 50 | 99 |
|  | 250 | 101 |
| C. Ex. 10 | 50 | 104 |
|  | 250 | 102 |

As can be seen in Table 16, the extract of Example 1 significantly promoted the growth of PC12 nerve cells, compared to the extract of Comparative Example 1 (from *Dioscorea* Rhizoma alone), the extract of Comparative Example 2 (from *Dioscorea nipponica* alone) or the extracts of Comparative Examples 3 to 10 (from mixtures of *Dioscorea* Rhizoma and *Dioscorea nipponica* at other weight ratios).

Thus, the herb extract of a mixture of 3.5:1 *Dioscorea* Rhizoma:*Dioscorea nipponica* in accordance with the present invention is proven to have a significant proliferative effect on nerve cells.

Test Example 6

Test for Phosphorylation of NGF Receptor in PC12 Nerve Cells

The herb extract of a mixture of 3.5:1 *Dioscorea* Rhizoma:*Dioscorea nipponica*, prepared in Example 1, was evaluated for its ability to promote the phosphorylation of NGF receptors in PC12 rat nerve cells.

For use in this test, PC12 nerve cells were seeded at the same density per well into plates and incubated for 24 hours. The cells were washed with PBS and cultured for 48 hours in culture media supplemented with the herb extracts of Example 1 or Comparative Examples 1 to 10 or NGF. Thereafter, phosphorylated TrkA (NGF receptor) were detected using Western blotting, and quantitatively analyzed on the basis of the thickness of the detected bands. The results are summarized in Table 17.

NGF signaling starts with the binding of NGF to its receptor (Trk-A), which results in the phosphorylation of the receptor. Thus, an increased level of phosphorylated NGF receptors means the amplification of the NGF signaling pathway.

As is apparent from data of Table 17, below, the extract of Example 1 induced a significant increase in the phosphorylation of NGF receptors, compared to the extract of Comparative Example 1 (from *Dioscorea* Rhizoma alone), the extract of Comparative Example 2 (from *Dioscorea nipponica* alone) or the extracts of Comparative Examples 3 to 10 (from mixtures of *Dioscorea* Rhizoma and *Dioscorea nipponica* at other weight ratios).

TABLE 17

Promotive Effect on Phosphorylation of NGF Receptor

| Group | Dose NGF (ng/ml) | Dose Combined Extract (μg/ml) | Relative Amount of Phosphorylated NGF (% of control) |
|---|---|---|---|
| Control |  |  | 100 |
| NGF | 2 | — | 241 |
|  | 50 | — | 337 |
| Ex. 1 + NGF | 2 | 200 | 309 |
|  |  | 500 | 389 |
| C. Ex. 1 + NGF | 2 | 200 | — |
|  |  | 500 | 232 |
| C. Ex. 2 + NGF | 2 | 200 | — |
|  |  | 500 | 229 |
| C. Ex. 3 + NGF | 2 | 200 | 268 |
|  |  | 500 | 299 |
| C. Ex. 4 + NGF | 2 | 200 | 255 |
|  |  | 500 | 287 |
| C. Ex. 5 + NGF | 2 | 200 | 254 |
|  |  | 500 | 274 |
| C. Ex. 6 + NGF | 2 | 200 | 248 |
|  |  | 500 | 277 |
| C. Ex. 7 + NGF | 2 | 200 | 251 |
|  |  | 500 | 268 |
| C. Ex. 8 + NGF | 2 | 200 | 239 |
|  |  | 500 | 287 |
| C. Ex. 9 + NGF | 2 | 200 | 249 |
|  |  | 500 | 296 |

TABLE 17-continued

Promotive Effect on Phosphorylation of NGF Receptor

| Group | Dose | | Relative Amount of Phosphorylated NGF (% of control) |
|---|---|---|---|
| | NGF (ng/ml) | Combined Extract (µg/ml) | |
| C. Ex. 10 + NGF | 2 | 200 | 244 |
| | | 500 | 280 |

Test Example 7

Test for Activity to Induce the Growth of Neurites in Rat-Derived DRG Nerve Cells The herb extract of a mixture of 3.5:1 *Dioscorea* Rhizoma:*Dioscorea nipponica*, prepared in Example 1, was evaluated for activity to promote the growth of neurites in DRG (Dorsal root ganglion) nerve cells obtained from rat embryos.

For use in this test, DRG nerve cells were seeded at the same density into plates and incubated for 24 hours. Thereafter, the cells were washed with PBS and cultured for 48 hours in a culture medium in the absence or presence of a combination of the extract of Example 1 or Comparative Examples 1 to 10, and NGF. The nerve cells in each group were observed under a microscope to measure the area of the neurites grown therein. Average values of the measurements are given in Table 18.

An increase in neurite area indicates that the nerve cells are activated to grow neurites. As can be seen in Table 18, below, the extract of Example 1 significantly increased a neurite area, compared to the extract of Comparative Example 1 (from *Dioscorea* Rhizoma alone), the extract of Comparative Example 2 (from *Dioscorea nipponica* alone) or the extracts of Comparative Examples 3 to 10 (from mixtures of *Dioscorea* Rhizoma and *Dioscorea nipponica* at other weight ratios).

TABLE 18

Promotive Effect on Formation of Neurites from DRG Nerve Cell

| Group | Dose | | Neurite Area of DRG Nerve Cell (µm$^2$) |
|---|---|---|---|
| | NGF (ng/ml) | Combined Extract (µg/ml) | |
| Control | | | 149 |
| NGF | 2 | — | 235 |
| | 50 | — | 461 |
| Ex. 1 + NGF | 2 | 30 | 291 |
| | | 100 | 502 |
| C. Ex. 1 + NGF | 2 | 30 | — |
| | | 100 | 234 |
| C. Ex. 2 + NGF | 2 | 30 | — |
| | | 100 | 236 |
| C. Ex. 3 + NGF | 2 | 30 | 264 |
| | | 100 | 288 |
| C. Ex. 4 + NGF | 2 | 30 | 259 |
| | | 100 | 271 |
| C. Ex. 5 + NGF | 2 | 30 | 241 |
| | | 100 | 294 |
| C. Ex. 6 + NGF | 2 | 30 | 232 |
| | | 100 | 301 |
| C. Ex. 7 + NGF | 2 | 30 | 269 |
| | | 100 | 288 |
| C. Ex. 8 + NGF | 2 | 30 | 257 |
| | | 100 | 279 |
| C. Ex. 9 + NGF | 2 | 30 | 241 |
| | | 100 | 266 |

TABLE 18-continued

Promotive Effect on Formation of Neurites from DRG Nerve Cell

| Group | Dose | | Neurite Area of DRG Nerve Cell (µm$^2$) |
|---|---|---|---|
| | NGF (ng/ml) | Combined Extract (µg/ml) | |
| C. Ex. 10 + NGF | 2 | 30 | 239 |
| | | 100 | 248 |

Taken together, the data obtained from Test Examples 1 to 7 demonstrate that the extract of Example 1 can significantly induce the elevation of in vivo NGF levels, the growth of nerve cells and neurites, the alleviation of pain, a symptom of diabetic neuropathy, and the prevention of histological neurodegeneration (the promotion of nerve regeneration), compared to the extract of Comparative Example 1 (from *Dioscorea Rhizoma* alone), the extract of Comparative Example 2 (from *Dioscorea nipponica* alone) or the extracts of Comparative Examples 3 to 10 (from mixtures of *Dioscorea* Rhizoma and *Dioscorea nipponica* at other weight ratios) and thus can be applied to pharmaceutical compositions and health aid foods for the prevention and treatment of diabetic peripheral neuropathy.

Below, a description will be given of illustrative, non-limiting examples of formulations containing the herb extract from a mixture of *Dioscorea* Rhizoma and *Dioscorea nipponica*.

Formulation Example 1. Preparation of Injection

| Extract of Example 1 | 100 mg |
|---|---|
| Sodium metabisulfite | 3.0 mg |
| Methylparaben | 0.8 mg |
| Propylparaben | 0.1 mg |
| Sterile water for injection | q.s. |

To a mixture of the ingredients was added sterile water to form a total volume of 2 mL, and the solution was loaded to a 2 mL ampule and sterilized to give an injection.

Formulation Example 2: Preparation of Tablet

| Extract of Example 1 | 200 mg |
|---|---|
| Lactose | 100 mg |
| Starch | 100 mg |
| Mg stearate | q.s. |

The ingredients were mixed and compressed into a tablet using a tableting method.

Formulation Example 3: Preparation of Capsule

| Extract of Example 1 | 100 mg |
|---|---|
| Lactose | 50 mg |
| Starch | 50 mg |
| Talc | 2 mg |
| Mg Stearate | q.s. |

The ingredients were mixed and loaded to a gelatin capsule according to a typical method to afford a capsule.

Formulation Example 4: Preparation of Liquid

| Extract of Example 1 | 1000 mg |
|---|---|
| sugar | 20 g |
| Isomeroase | 20 g |
| Lemon Flavor | q.s. |

Purified water added to form a total volume of 100 mL.

The above ingredients were mixed, loaded into a 100 mL brown vial and sterilized to afford a liquid formulation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for treating a diabetic peripheral neuropathy in a subject in need thereof, comprising administering to the subject an effective amount of a pharmaceutical composition comprising an extract of a mixture comprising *Dioscorea* Rhizoma and a rhizome of *Dioscorea nipponica*, wherein the mixture is at a weight ratio of 3.5:1 (w/w) of the *Dioscorea* Rhizoma and the rhizome of *Dioscorea nipponica*.

2. The method of claim 1, wherein the diabetic peripheral neuropathy exhibits a symptom selected from the group consisting of a burning discomfort, a stingy ache, soreness, a straining feeling, loss of tactile sensation, vibratory sensation or temperature sensation, and a combination thereof.

3. The method of claim 1, wherein the *Dioscorea* Rhizoma is a rhizome of *Dioscorea batatas* Decaisne or *Dioscorea japonica* Thunberg.

4. The method of claim 3, wherein the *Dioscorea* Rhizoma is steamed and dried.

5. The method of claim 1, wherein the rhizome of *Dioscorea nipponica* is a rhizome of *Dioscorea nipponica* Makino.

6. The method of claim 1, wherein the pharmaceutical composition further comprises a suitable carrier, excipient or diluent selected from the group consisting of lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

7. The method of claim 1, wherein the pharmaceutical composition is in a solid form.

8. The method of claim 1, wherein the pharmaceutical composition is in a liquid form.

9. The method of claim 1, wherein the pharmaceutical composition further comprises magnesium stearate and wherein the pharmaceutical composition is in an injectable form.

10. The method of claim 1, wherein the pharmaceutical composition further comprises magnesium stearate and wherein the pharmaceutical composition is in a tablet form.

11. The method of claim 1, wherein the pharmaceutical composition further comprises magnesium stearate and wherein the pharmaceutical composition is in a capsule form.

12. The method of claim 1, wherein the pharmaceutical composition further comprises magnesium stearate and wherein the pharmaceutical composition is in a liquid form.

13. The method of claim 1, wherein the pharmaceutical composition is administered at a dose from 0.01 g/kg to 10 g/kg.

14. The method of claim 1, wherein the pharmaceutical composition is administered orally, intrarectally, intravenously, intramuscularly, hypodermically, endometrially, or intracerebroventicularly.

15. The method of claim 1, wherein the pharmaceutical composition further comprises polyvinyl pyrrolidone.

16. The method of claim 1, wherein the pharmaceutical composition further comprises polyvinyl pyrrolidone and wherein the pharmaceutical composition is in a tablet form.

* * * * *